(12) United States Patent
Gohno et al.

(10) Patent No.: US 7,327,824 B2
(45) Date of Patent: Feb. 5, 2008

(54) RADIATION TOMOGRAPHY APPARATUS AND RADIATION TOMOGRAPHY METHOD THEREOF

(75) Inventors: Makoto Gohno, Tokyo (JP); Masatake Nukui, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 415 days.

(21) Appl. No.: 10/924,097

(22) Filed: Aug. 23, 2004

(65) Prior Publication Data

US 2005/0053191 A1 Mar. 10, 2005

(30) Foreign Application Priority Data

Sep. 8, 2003 (JP) .............................. 2003-315505

(51) Int. Cl.
 *A61B 6/03* (2006.01)
(52) U.S. Cl. ......................................... 378/19; 250/366
(58) Field of Classification Search .................. 378/19; 250/366, 367, 369
See application file for complete search history.

(56) References Cited

U.S. PATENT DOCUMENTS

| | | |
|---|---|---|
| 4,670,840 A | 6/1987 | Freundlich |
| 4,897,788 A | 1/1990 | King |
| 5,099,505 A | 3/1992 | Seppi et al. |
| 6,067,342 A | 5/2000 | Gordon |
| 6,215,843 B1 | 4/2001 | Saito et al. |
| 6,438,198 B1 | 8/2002 | Kohler |
| 6,859,514 B2 * | 2/2005 | Hoffman ...................... 378/19 |
| 2001/0002699 A1 | 6/2001 | Such et al. |
| 2007/0007447 A1 * | 1/2007 | Spahn ...................... 250/252.1 |

FOREIGN PATENT DOCUMENTS

| | | |
|---|---|---|
| JP | 09-066052 | 3/1997 |
| JP | 09-234197 | 9/1997 |
| JP | 11-253432 | * 9/1999 |

OTHER PUBLICATIONS

European Patent Office Search Report; 154281/10175; 04255382. 6-2305-; GE Medical Systems Global Technology Company LLC; 3 pgs.

* cited by examiner

*Primary Examiner*—Edward J. Glick
*Assistant Examiner*—John M. Corbett
(74) *Attorney, Agent, or Firm*—Armstrong Teasdale LLP (57) ABSTRACT

A method and apparatus for reducing the contrast of a tomographic image due to crosstalk and the occurrence of artifacts and improve the quality of the tomographic image. Detection data are subjected to fitting processing in such a manner that, of the data generated by an X-ray detected by X-ray detection elements disposed in array form in a plurality of X-ray detection modules disposed adjacent to one another, first detection data generated by the X-ray detected by X-ray detection elements adjacent to a boundary between the plurality of X-ray detection modules are adapted to waveform data based on second detection data generated by the X-ray detected by X-ray detection elements lying around the adjacent X-ray detection elements.

13 Claims, 9 Drawing Sheets

| A11 | A21 | A31 | A41 | B11 | B21 | B31 | B41 |
|-----|-----|-----|-----|-----|-----|-----|-----|
| A12 | A22 | A32 | A42 | B12 | B22 | B32 | B42 |
| A13 | A23 | A33 | A43 | B13 | B23 | B33 | B43 |
| A14 | A24 | A34 | A44 | B14 | B24 | B34 | B44 |
| A15 | A25 | A35 | A45 | B15 | B25 | B35 | B45 |
| A16 | A26 | A36 | A46 | B16 | B26 | B36 | B46 |
| A17 | A27 | A37 | A47 | B17 | B27 | B37 | B47 |
| A18 | A28 | A38 | A48 | B18 | B28 | B38 | B48 |
| A1  | A2  | A3  | A4  | B1  | B2  | B3  | B4  |

| A11 | A21 | A31 | A'41 | B'11 | B21 | B31 | B41 |
|-----|-----|-----|------|------|-----|-----|-----|
| A12 | A22 | A32 | A'42 | B'12 | B22 | B32 | B42 |
| A13 | A23 | A33 | A'43 | B'13 | B23 | B33 | B43 |
| A14 | A24 | A34 | A'44 | B'14 | B24 | B34 | B44 |
| A15 | A25 | A35 | A'45 | B'15 | B25 | B35 | B45 |
| A16 | A26 | A36 | A'46 | B'16 | B26 | B36 | B46 |
| A17 | A27 | A37 | A'47 | B'17 | B27 | B37 | B47 |
| A18 | A28 | A38 | A'48 | B'18 | B28 | B38 | B48 |
| A1  | A2  | A3  | A4   | B1   | B2  | B3  | B4  |

| A11 | A21 | A31 | A41 | B11 | B21 | B31 | B41 |
|-----|-----|-----|-----|-----|-----|-----|-----|
| A12 | A22 | A32 | A42 | B12 | B22 | B32 | B42 |
| A13 | A23 | A33 | A43 | B13 | B23 | B33 | B43 |
| A14 | A24 | A34 | A44 | B14 | B24 | B34 | B44 |
| A15 | A25 | A35 | A45 | B15 | B25 | B35 | B45 |
| A16 | A26 | A36 | A46 | B16 | B26 | B36 | B46 |
| A17 | A27 | A37 | A47 | B17 | B27 | B37 | B47 |
| A18 | A28 | A38 | A48 | B18 | B28 | B38 | B48 |
| A1  | A2  | A3  | A4  | B1  | B2  | B3  | B4  |

| A11 | A21 | A31 | A'''41 | B'''11 | B21 | B31 | B41 |
|-----|-----|-----|--------|--------|-----|-----|-----|
| A12 | A22 | A32 | A'''42 | B'''12 | B22 | B32 | B42 |
| A13 | A23 | A33 | A'''43 | B'''13 | B23 | B33 | B43 |
| A14 | A24 | A34 | A'''44 | B'''14 | B24 | B34 | B44 |
| A15 | A25 | A35 | A'''45 | B'''15 | B25 | B35 | B45 |
| A16 | A26 | A36 | A'''46 | B'''16 | B26 | B36 | B46 |
| A17 | A27 | A37 | A'''47 | B'''17 | B27 | B37 | B47 |
| A18 | A28 | A38 | A'''48 | B'''18 | B28 | B38 | B48 |
| A1  | A2  | A3  | A4     | B1     | B2  | B3  | B4  |

23A    K    23B

RADIATION TOMOGRAPHY APPARATUS AND RADIATION TOMOGRAPHY METHOD THEREOF

CROSS REFERENCE TO RELATED APPLICATIONS

This application claims the benefit of Japanese Application No. 2003-315505 filed Sep. 8, 2003.

BACKGROUND OF THE INVENTION

The present invention relates to a radiation tomography apparatus and a radiation tomography method thereof.

An X-ray CT (Computed Tomography) apparatus that generates an image of a tomographic plane of a subject to be imaged using an X-ray corresponding to radiation has been known as a radiation tomography apparatus. The X-ray CT apparatus has been used in widespread applications such as medical and industrial applications with a human body and an object as subjects to be imaged.

The X-ray CT apparatus scans the periphery of a subject to be imaged with a subject's body axis direction as the axis and applies X-rays to the subject from a plurality of view directions through an X-ray tube. The X-rays radiated from the X-ray tube are blocked or cut off thereby forming an X-ray so as to be applied to an imaging area of the subject. The X-rays transmitted through the subject from the plural view directions via the collimator are detected by an X-ray detector array for each of the view directions, and a tomographic image corresponding to the imaging area of the subject is reconstructed and generated based on detection data generated by the X-rays detected by the X-ray detector array.

A region of a subject to be imaged and the purpose of imaging it have been diversified for the X-ray CT apparatus. There has thus been a demand for an improvement in the image quality such as resolution and speeding-up of its imaging. In order to meet such a demand, the X-ray CT apparatus has an X-ray detector array in which a plurality of X-ray detection elements are arranged in array form so as to be capable of obtaining a plurality of tomographic images while the periphery of the subject is being scanned with one rotation. The X-ray detector array has X-ray detection modules in which X-ray detection elements for detecting an X-ray are arranged plural in array form. In order to facilitate its manufacture, a plurality of X-ray detection modules are configured so as to be disposed adjacent to both a channel direction and a body axial direction.

Since the plurality of X-ray detection elements are disposed adjacent to one another in the X-ray detector array in which the plurality of X-ray detection elements are arranged in array form, crosstalk might occur among the X-ray detection elements due to a detected X-ray. Therefore, when a tomographic image is reconstructed and generated based on detection data containing the crosstalk, there might be cases where in the X-ray CT apparatus, a reduction in the contrast of a tomographic image and artifacts occurred and the quality of an image was deteriorated.

In order to prevent the deterioration of the image quality due to the crosstalk, various methods have heretofore been proposed. In the prior art, for example, the generated amounts of crosstalk are determined every X-ray detection elements in advance, and detection data are corrected using the determined generated amounts of crosstalk (refer to a patent document 1, for example).

[Patent Document 1]Specification of U.S. Pat No. 4,897,788

Since, however, the periphery of a phantom was scanned with the body axial direction as the axis in the prior art, it was easy to determine the generated amounts of crosstalk every X-ray detection elements in the channel direction. However, it was difficult to obtain the generated amounts of crosstalk in the body axial direction. Therefore, the prior art encountered difficulties in preventing deterioration of the quality of an image due to the crosstalk in the body axial direction. Since there are cut lines or breaks between the adjacent X-ray detection elements at the boundaries among the plurality of X-ray detection modules as viewed in the boy axial direction in particular, the X-ray detection elements lying in the neighborhood of the boundaries of the X-ray detection modules as viewed in the body axial direction and the X-ray detection elements lying therearound are different from one another in the number of the X-ray detection elements respectively adjacent thereto, and profiles of the generated amounts of crosstalk in the body axial direction become discontinuous. Therefore, a reduction in the contrast of a tomographic image and the occurrence of artifacts happened noticeably.

Since the generated amount of crosstalk obtained in advance is used without using the generated amount of crosstalk at the actual acquisition of detection data in the prior art, it was not possible to correct the image quality with higher accuracy and hence sufficiently improve the image quality.

SUMMARY OF THE INVENTION

Therefore, an object of the present invention is to provide a radiation tomography apparatus capable of preventing a reduction in the contrast of a tomographic image due to crosstalk and the occurrence of artifacts and improving the quality of a tomographic image, and a radiation tomography method thereof.

In order to attain the above object, a radiation tomography apparatus of the present invention comprises radiation irradiating means for irradiating an imaging area of a subject to be imaged with radiation, radiation detecting means having first and second radiation detection modules in which radiation detection elements detecting the radiation transmitted through the imaging area of the subject are disposed in array form, the first and second radiation detection modules being arranged adjacent to each other, and fitting processing means for effecting fitting processing on detection data in such a manner that, of the detection data generated by the radiation detected by the radiation detecting means, first detection data generated by the radiation detected by first radiation detection elements corresponding to the radiation detection elements adjacent to a boundary between the first and second radiation detection modules are adapted to waveform data based on second detection data generated by the radiation detected by second radiation detection elements corresponding to the radiation detection elements lying around the first radiation detection elements.

In the above radiation tomography apparatus of the present invention, the radiation is applied to the imaging area of the subject, and the radiation transmitted through the imaging area of the subject is detected by the radiation detection elements disposed in array form in the first and second radiation detection modules disposed adjacent to each other. Then, the detection data are subjected to the fitting processing in such a manner that, of the detection data generated by the radiation detected by the radiation detecting means, the first detection data generated by the radiation detected by the first radiation detection elements corresponding to the radiation detection elements adjacent to the boundary between the first and second radiation detection modules are adapted to the waveform data based on the second detection data generated by the radiation detected by the second radiation detection elements corresponding to the radiation detection elements lying around the first radiation detection elements.

In order to achieve the above object, a radiation tomography method of the present invention, using a radiation tomography apparatus having radiation irradiating means for irradiating an imaging area of a subject to be imaged with radiation, and radiation detecting means having first and second radiation detection modules in which radiation detection elements detecting the radiation transmitted through the imaging area of the subject are disposed in array form, the first and second radiation detection modules being arranged adjacent to each other, comprises a fitting processing process for performing fitting processing on detection data in such a manner that, of the detection data generated by the radiation detected by the radiation detecting means, first detection data generated by the radiation detected by first radiation detection elements corresponding to the radiation detection elements adjacent to a boundary between the first and second radiation detection modules are adapted to waveform data based on second detection data generated by the radiation detected by second radiation detection elements corresponding to the radiation detection elements lying around the first radiation detection elements.

In the above radiation tomography method of the present invention, the detection data generated by the radiation applied to the imaging area of the subject, transmitted through the imaging area and detected by the radiation detection elements disposed in array form in the first and second radiation detection modules disposed adjacent to each other are subjected to the fitting processing in such a manner that the first detection data of the detection data, generated by the radiation detected by the first radiation detection elements corresponding to the radiation detection elements adjacent to the boundary between the first and second radiation detection modules are adapted to the waveform data based on the second detection data generated by the radiation detected by the second radiation detection elements corresponding to the radiation detection elements lying around the first radiation detection elements.

According to the present invention, a radiation tomography apparatus capable of preventing a reduction in the contrast of a tomographic image due to crosstalk and the occurrence of artifacts and improving the quality of a tomographic image, and a radiation tomography method thereof can be provided.

Further objects and advantages of the present invention will be apparent from the following description of the preferred embodiments of the invention as illustrated in the accompanying drawings.

BRIEF DESCRIPTION OF THE DRAWINGS

FIG. 4 is a diagram showing the interrelationship among an X-ray tube, a collimator and an X-ray detector array employed in the X-ray CT apparatus used as the radiation tomography apparatus according to the embodiment 1 of the present invention, wherein FIG. 4($a$) is a diagram showing a state in which a body axial direction is seen from the side as defined as a visual line, and FIG. 4($b$) is a diagram showing a state in which a channel direction x is seen from the side as defined as a visual line, respectively.

DETAILED DESCRIPTION OF THE INVENTION

Embodiments of the present invention will hereinafter be described in detail with reference to the accompanying drawings.

Embodiment 1

Figure 1:
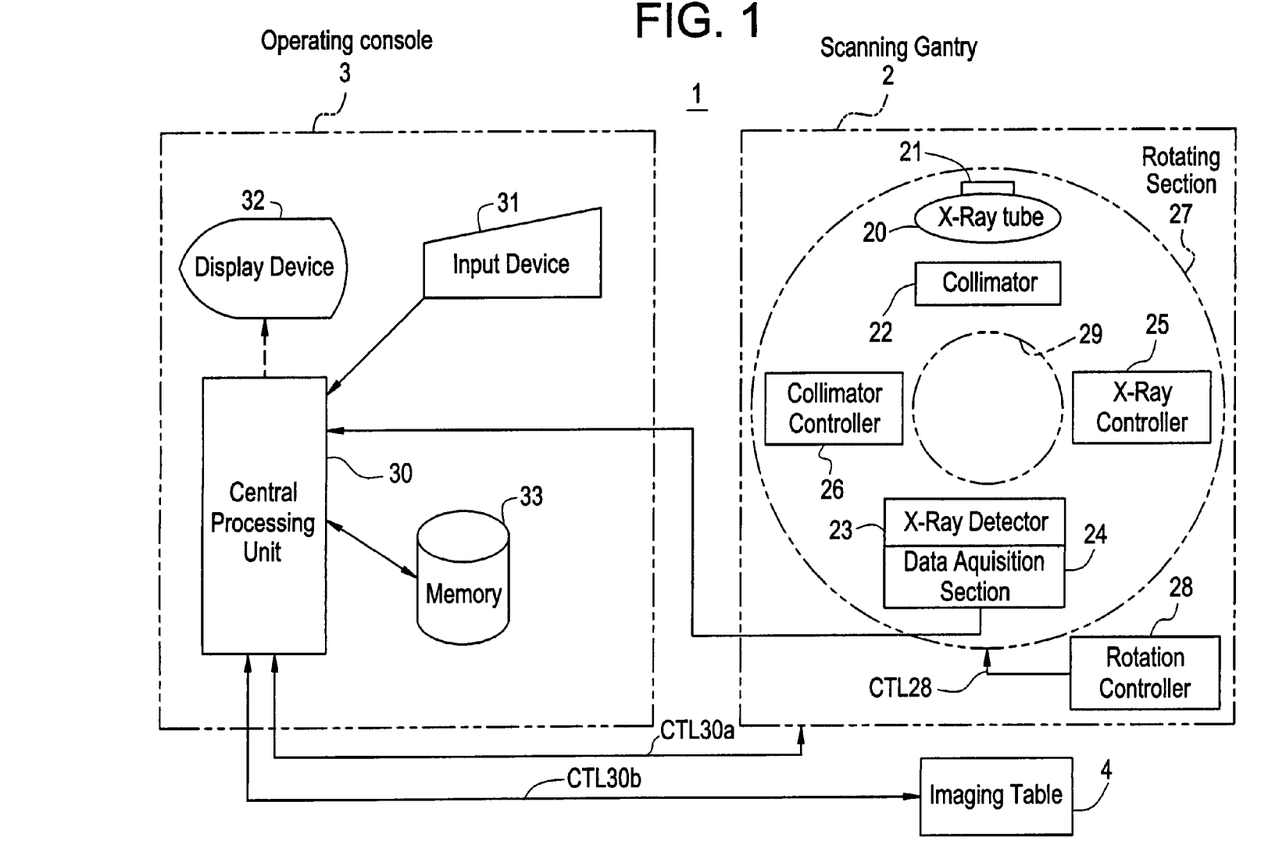
FIG. 1 is a block diagram showing an overall configuration of an X-ray CT apparatus used as a radiation tomography apparatus according to an embodiment 1 of the present invention.
Figure 2:
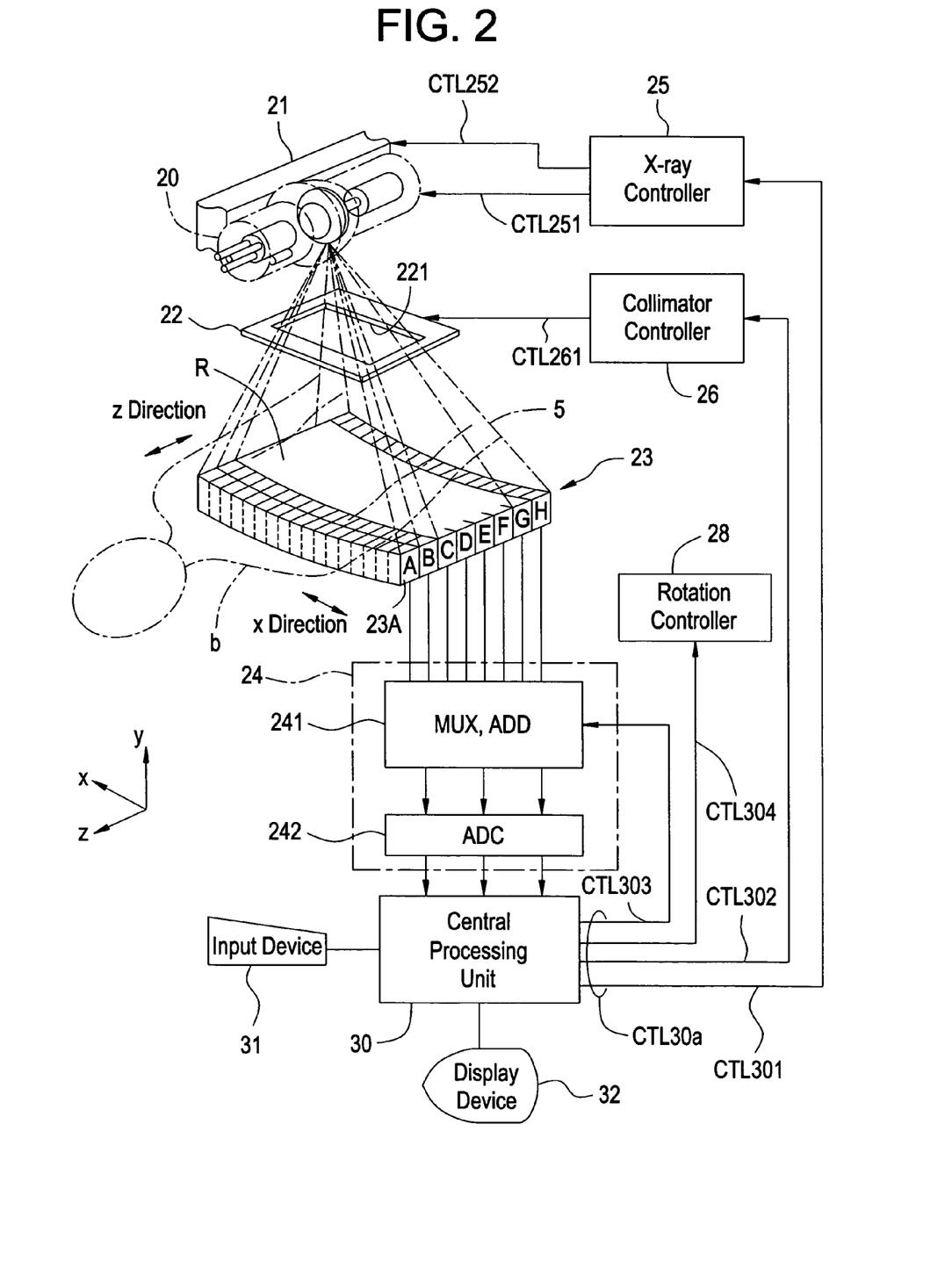
FIG. 2 is a configurational diagram showing an essential part of the X-ray CT apparatus used as the radiation tomography apparatus according to the embodiment 1 of the present invention.

FIG. 1 is a block diagram showing an overall configuration of an X-ray CT apparatus 1 used as a radiation tomography apparatus according to an embodiment 1 of the present invention. FIG. 2 is a configurational diagram illustrating an essential part of the X-ray CT apparatus 1 used as the radiation tomography apparatus according to the embodiment 1 of the present invention.

As shown in FIG. 1, the X-ray CT apparatus 1 according to the present embodiment includes a scanning gantry 2, an operating console 3 and an imaging table 4.

The scanning gantry 2 includes an X-ray tube 20, an X-ray tube moving section 21, a collimator 22, an X-ray detector array 23, a data acquisition section 24, an X-ray controller 25, a collimator controller 26, a rotating section 27 and a rotation controller 28 as principal components. Here, the X-ray tube 20 and the X-ray detector array 23 are opposed to each other with an X-ray irradiation space 29 interposed therebetween.

Incidentally, a radiation irradiating means according to the present invention is comprised of the X-ray tube 20 of the scanning gantry 2, whereas a radiation detecting means according to the present invention is constituted of the X-ray detector array 23 thereof. A rotating means according to the present invention is comprised of the rotating section 27 of the scanning gantry 2.

The X-ray tube 20 irradiates an imaging area of a subject 6 to be imaged with an X-ray 5 having a predetermined intensity through the collimator 22 on the basis of a control signal CTL251 transmitted from the X-ray controller 25.

The X-ray tube moving section 21 moves the center of radiation of the X-ray tube 20 in the direction (direction orthogonal to the sheet shown in FIG. 1 and z direction of FIG. 2) of a body axis of the subject 6 placed on the imaging table 4 lying in the X-ray irradiation space 29 of the scanning gantry 2.

The collimator 22 is placed between the X-ray tube 20 and the X-ray detector array 23 and blocks or cuts off the X-ray 5 radiated from the X-ray tube 20 as viewed in a channel direction x and a subject's body axial direction z, based on a control signal CTL261 supplied from the collimator controller 26, respectively, to shape it in the form of a cone-shaped X-ray 5 having predetermined widths as viewed in the channel direction x and body axial direction z, thereby adjusting an irradiation range of the X-ray. Here, the irradiation range of the X-ray 5 is set by adjusting the degree of opening of an aperture of the collimator 22, based on the control signal CTL261. The degree of opening of the aperture of the collimator 22 is adjusted by, for example, independently moving two plates respectively provided in the channel direction x and the body axial direction z.

The X-ray detector array 23 includes eight X-ray detection modules 23A, 23B, 23C, 23D, 23E, 23F, 23G, and 23H in which a plurality of X-ray detection elements are disposed in array form, respectively. Eight X-ray detection modules 23A, 23B, 23C, 23D, 23E, 23F, 23G and 23H are placed in parallel so as to adjoin in the body axial direction z in order of from a column A to a column H.

Incidentally, a radiation detection module according to the present invention is constituted of the X-ray detection modules 23A, 23B, 23C, 23D, 23E, 23F, 23G and 23H of the X-ray detector array 23. For instance, the X-ray detection modules lying in the columns A and B correspond to first and second radiation detection modules respectively. A radiation detection element according to the present invention is constituted of each of X-ray detection elements 23a.

Figure 3:
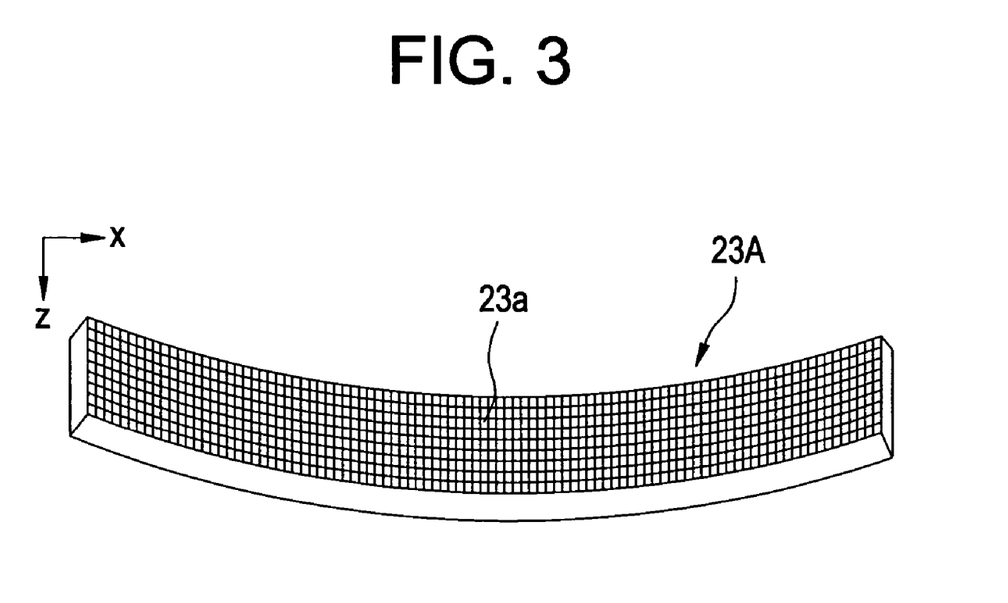
FIG. 3 is a configurational diagram of an X-ray detection module employed in the X-ray CT apparatus used as the radiation tomography apparatus according to the embodiment 1 of the present invention.

FIG. 3 is a configurational diagram showing the X-ray detection module 23A corresponding to the column A, of the eight X-ray detection modules 23A, 23B, 23C, 23D, 23E, 23F, 23G and 23H constituting the X-ray detector array 23 employed in the present embodiment. As shown in FIG. 3, the X-ray detection module 23A includes the X-ray detection elements 23a laid out in array form in the channel direction x and the body axial direction z. A plurality of the X-ray detection elements 23a arranged on a two-dimensional basis form an X-ray incident plane bent in the form of a cylindrical concave surface as a whole. Here, for example, 1000 X-ray detection elements 23a are arranged in the channel direction x, and, for example, eight X-ray detection elements 23a are arranged in the subject's body axial direction z. Incidentally, the X-ray detection modules 23B, 23C, 23D, 23E, 23F, 23G and 23H corresponding to the columns B to H are also similar to the X-ray detection module 23A corresponding to the column A shown in FIG. 3. Therefore, the X-ray detector array 23 having the eight having the eight X-ray detection modules 23A, 23B, 23C, 23D, 23E, 23F, 23G and 23H is capable of generating detection data corresponding to 32 in total where, for example, four detection data are generated per module.

Each of the X-ray detection elements 23a includes a combination of a scintillator and a photo diode, for example. Incidentally, the X-ray detection element 23a is not limited to it but may be a semiconductor X-ray detection element using Cadmium Telluride (CdTe) or the like or an ionization chamber type X-ray detection element 23a using xenon (Xe) gas.

In the present embodiment, first detection data are generated from X-ray's row data detected by X-ray detection elements 23a adjacent to the boundaries among the plurality of X-ray detection modules 23A, 23B, 23C, 23D, 23E, 23F, 23G and 23H. Second detection data are generated from X-ray's row data detected by X-ray detection elements 23a lying around the X-ray detection elements 23a by which the row data corresponding to the first detection data have been obtained. In the X-ray detection modules 23A and 23B corresponding to A and B, for example, first detection data is obtained from one X-ray detection element 23a located in a position closest to the boundary between the X-ray detection modules 23A and 23B corresponding to A and B. Further, second detection data is obtained using three X-ray detection elements 23a close to the X-ray detection element 23a for obtaining the first detection data as viewed in the body axial direction. Since breaks or cut lines exist between the adjacent X-ray detection elements 23a at the boundaries of the plurality of X-ray detection modules 23A, 23B, 23C, 23D, 23E, 23F, 23G and 23H as viewed in the body axial direction z, and the X-ray detection elements 23a lying in the neighborhood of the boundaries among the X-ray detection modules 23A, 23B, 23C, 23D, 23E, 23F, 23G and 23H as viewed in the body axial direction z and the X-ray detection elements 23a lying therearound are different from one another in the number of the X-ray detection elements 23a respectively adjacent thereto, profiles of the generated amounts of crosstalk in the body axial direction become discontinuous. Therefore, the first detection data contains the generated amount of crosstalk different from the second detection data.

Incidentally, a first radiation detection element according to the present invention is constituted of each of the X-ray detection elements 23a which are adjacent to the boundaries of the plurality of X-ray detection modules 23A, 23B, 23C, 23D, 23E, 23F, 23G and 23H of the X-ray detector array 23 and detect the X-ray defined as the first detection data. Also a second radiation detection element according to the present invention is comprised of each of the X-ray detection elements 23a lying around the X-ray detection elements 23a that detect the X-ray to be assumed as the first detection data.

Figure 4A:
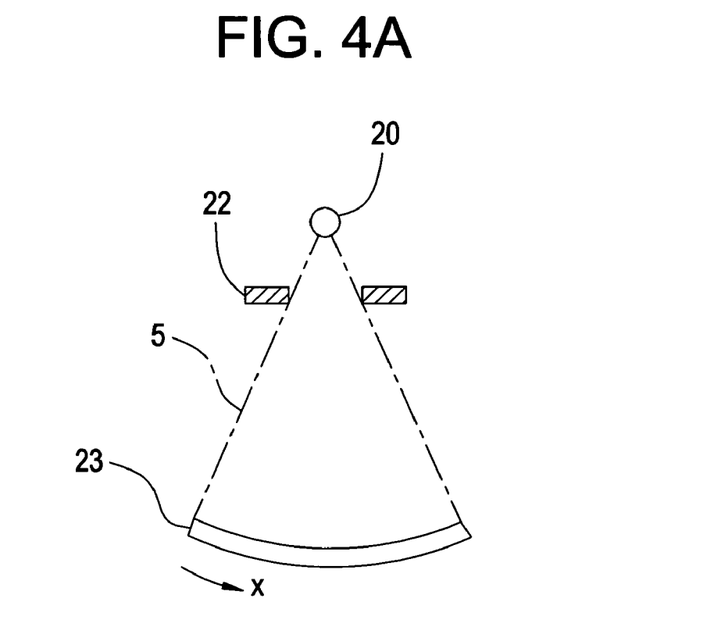
Figure 4B:
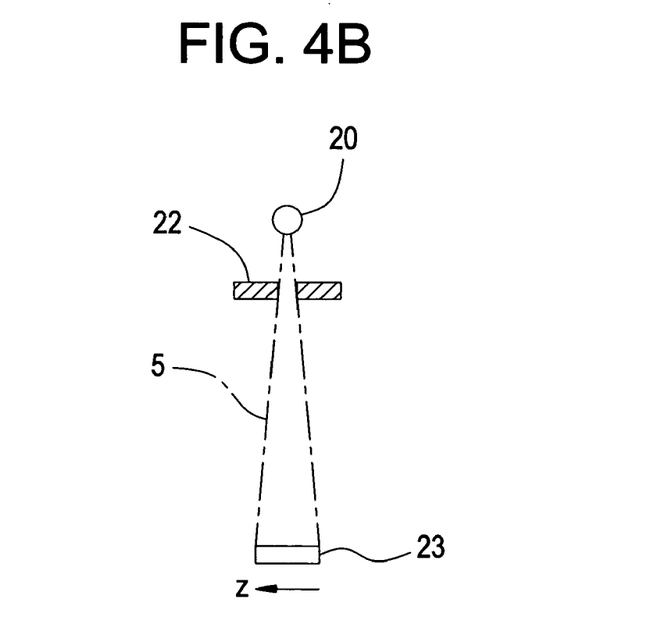
Figure 5:
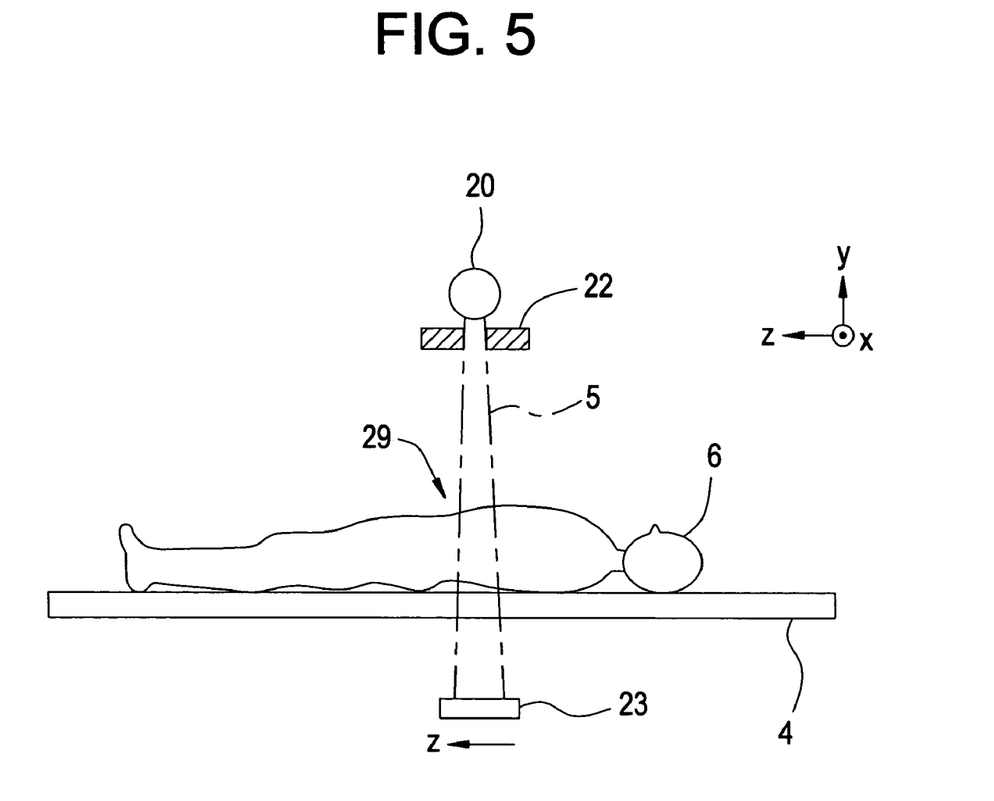
FIG. 5 is a diagram showing the interrelationship among the X-ray tube, the collimator and the X-ray detector array employed in the X-ray CT apparatus used as the radiation tomography apparatus according to the embodiment 1 of the present invention and shows the manner in which a subject to be imaged is imaged in a state in which the channel direction is seen from the side as defined as a visual line.

FIGS. 4 and 5 are respectively diagrams showing the interrelationship among the X-ray tube 20, the collimator 22 and the X-ray detector array 23. In FIG. 4, FIG. 4(a) is a diagram showing a state in which the subject's body axial direction z is seen from the side as defined as a visual line, and FIG. 4(b) is a diagram showing a state in which the channel direction x is seen from the side as defined as a visual line, respectively. FIG. 5 is a diagram showing the manner in which a subject 6 to be imaged is shot or imaged in a state in which the channel direction x is seen from the side as defined as a visual line in a manner similar to FIG. 4(b).

As shown in FIGS. 4(a) and 4(b), an X-ray 5 radiated from the X-ray tube 20 is formed so as to assume a cone-shaped X-ray 5 having predetermined cone angles by the collimator 22, which in turn is applied to a predetermined area of the X-ray detector array 23. When the subject 6 is imaged as shown in FIG. 5, the subject 6 placed on the imaging table 4 is carried in the X-ray irradiation space 29, where the periphery of the subject 6 is scanned with the body axial direction of the subject 6 as the axis and the X-ray 5 is applied to an imaging area of the subject 6 through the X-ray tube 5. Then, the X-ray 5 radiated from the X-ray tube 20 passes through the subject 6 via the collimator 22 and is detected by the X-ray detector array 23.

The data acquisition section 24 collects row data detected by the individual X-ray detection elements 23a in the X-ray detector array 23 and outputs it to the operating console 3. As shown in FIG. 2, the data acquisition section 24 has, for example, a selection/addition switching circuit (MUX, ADD) 241 and an analog-digital converter (ADC) 242. The selection/addition switching circuit 241 selects the row data detected by the X-ray detection elements 23a of the X-ray detector array 23 in accordance with a control signal CTL303 transmitted from a central processing unit 30 of the operating console 3 or changes their combinations and adds them together, and outputs the result thereof to the analog-digital converter 242. The analog-digital converter 242 converts the row data selected or added together in arbitrary combinations in the selection/addition switching circuit 241 from an analog signal to a digital signal, followed by being outputted to the central processing unit 30 of the operating console 3.

The X-ray controller 25 outputs a control signal CTL251 to the X-ray tube 20 in accordance with a control signal CTL301 sent from the central processing unit 30 of the operating console 3 to thereby control X-ray radiation. Also the X-ray controller 25 outputs a control signal CTL252 to the X-ray tube moving section 21 in accordance with the control signal CT301 supplied from the central processing unit 30 of the operating console 3 to move the center of radiation of the X-ray tube 20 by a distance corresponding to instructions in the subject's body axial direction z.

The collimator controller 26 outputs a control signal CTL261 to the collimator 22 in accordance with a control signal CTL302 supplied from the central processing unit 30 of the operating console 3 to adjust the degree of opening of the aperture 221 of the collimator 22 and allow the X-ray 5 radiated from the X-ray tube 20 to be formed, thereby irradiating a desired area of the X-ray detector array 23 with the X-ray 5.

The rotating section 27 is rotated in a predetermined direction based on a control signal CTL28 sent from the rotation controller 28. The rotation section 27 is equipped with the X-ray tube 20, the X-ray tube moving section 21, the collimator 22, the X-ray detector array 23, the data acquisition section 24, the X-ray controller 25 and the collimator controller 26. These components vary in position relation with respect to the subject 6 carried in the X-ray irradiation space 29 with the rotation of the rotating section 27. By rotating the rotating section 27, the X-rays are radiated from a plurality of view directions with the body axial direction of the subject 6 as the axis and the X-ray 5 transmitted through the subject 6 is detected.

The rotation controller 28 outputs the control signal CTL28 to the rotating section 27 in accordance with a control signal CTL304 outputted from the central processing unit 30 of the operating console 3 to thereby rotate the rotating section 27 by a desired number of revolutions in a predetermined direction.

The operating console 3 has as main components the central processing unit 30, an input device 31, a display device 32 and a memory device 33.

Incidentally, here, the central processing unit 30 includes a fitting processing means and a tomographic image generating means according to the present invention. The display device 32 constitutes a display means according to the present invention.

The central processing unit 30 comprises a microcomputer or the like, for example and has programs corresponding to various functions. The central processing unit 30 outputs a control signal CTL30b to the imaging table 4 in accordance with instructions inputted from the input device 31 in order to cause the imaging table 4 with the subject 6 placed thereon to be carried in the X-ray irradiation space 29 of the scanning gantry 2 or be carried out therefrom.

The central processing unit 30 outputs the control signal CTL304 to the rotating controller 28 of the scanning gantry 2 in response to multi-slice scan start instructions inputted from the input device 31 to thereby rotate the rotating section 27 of the scanning gantry 2 in a predetermined direction at the number of revolutions corresponding to instructions.

The central processing unit 30 outputs the control signal CTL301 to the X-ray controller 25 to cause the X-ray tube 20 of the scanning gantry 2 to radiate the X-ray 5.

The central processing unit 30 outputs the control signal CTL301 to the X-ray controller 25 in response to information about an imaging area of the subject 6, which is inputted from the input device 31, to thereby move the center of radiation of the X-ray tube 20 by a distance corresponding to instructions in the body axial direction z. At this time, the central processing unit 30 outputs the control signal CTL302 for controlling the collimator 22 so as to provide the predetermined degree of opening of the aperture to the collimator controller 26 in order to radiate the X-ray 5 into a predetermined range.

The central processing unit 30 outputs the control signal CTL303 to the selection/addition switching circuit 241 of the data acquisition section 24 so as select row data obtained by the X-ray detection elements 23a in the X-ray detector array 23 or change their combinations and add the same together, in accordance with information about the imaging area of the subject 6, which is inputted from the input device 31. Also the central processing unit 30 effects pre-treatment such as sensitivity correction on the row data collected by the data acquisition section 24 to thereby generate detection data.

The central processing unit 30 has a program that functions as a fitting processing means. The fitting processing means performs fitting processing on the detection data so as to cause first detection data generated by the X-ray detection elements 23a adjacent to the boundaries of the plurality of X-ray detection modules to be adapted to waveform data based on second detection data generated by the X-ray detection elements 23a lying around the X-ray detection elements 23a having generated the first detection data.

In the present embodiment, the fitting processing means performs fitting processing through the use of the first detection data and the second detection data. For instance, the fitting processing means give weighting factors to the first detection data and the second detection data so that they are adapted to waveform data expressed in a polynomial equation derived from a least squares error reference, using the first detection data and the second detection data to normalize the first detection data, thereby performing fitting processing on the detection data. Incidentally, the details of the fitting processing using the first detection data and the second detection data will be described later.

Further, the central processing unit 30 has a program that functions as a tomographic image generating means and performs an image reconstruction, based on the detection data from a plurality of view directions to generate plural tomographic images. Here, the first detection data and second detection data subjected to the fitting processing are used as the detection data. For example, a filtered back projection method is used in the image reconstruction of the central processing unit 30. The central processing unit 30 causes the display device 32 to display a reconstructed image thereon.

The input device 31 is provided to input information such as imaging conditions to the central processing unit 30 and is constituted of, for example, a keyboard or a mouse. Incidentally, the input device 31 may be connected to the scanning gantry 2 or the imaging table 4.

The display device 32 displays a reconstructed and produced tomographic image and other various information thereon based on a command issued from the central processing unit 30.

The memory device 33 stores various data, reconstructed images and programs therein. The stored data is accessed by the central processing unit 30 as needed.

An X-ray tomography method using the X-ray CT apparatus 1 according to the present embodiment will next be described.

Figure 6A:
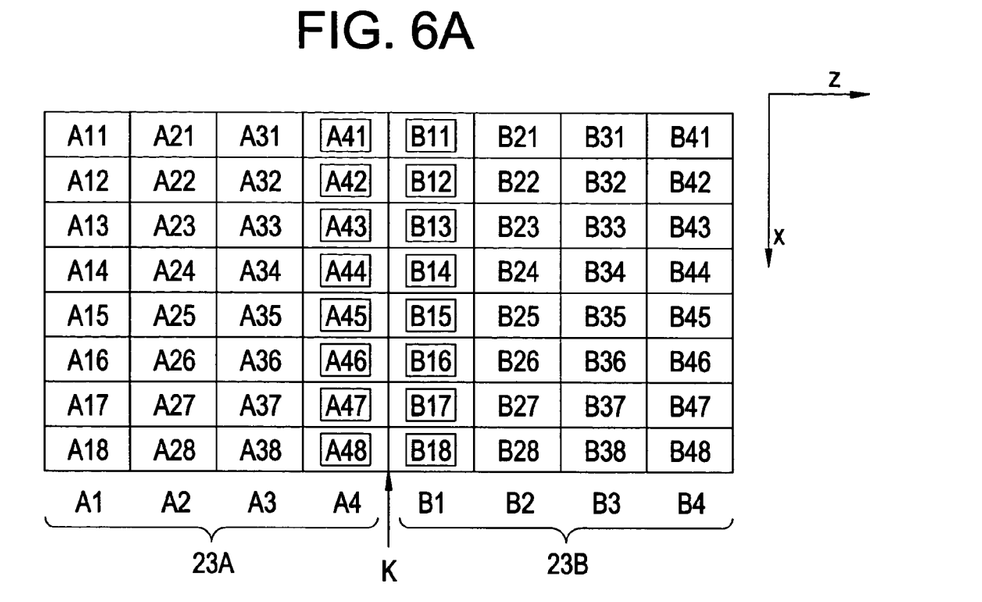
FIG. 6 is a diagram showing detection data generated based on an X-ray detected by sections of two X-ray detection modules corresponding to A and B, of a plurality of X-ray detection modules of the X-ray detector array in X-ray CT apparatus used as the radiation tomography apparatus according to the embodiment 1 of the present invention, which two modules are arranged in parallel adjacent to each other in the body axial direction.
Figure 6B:
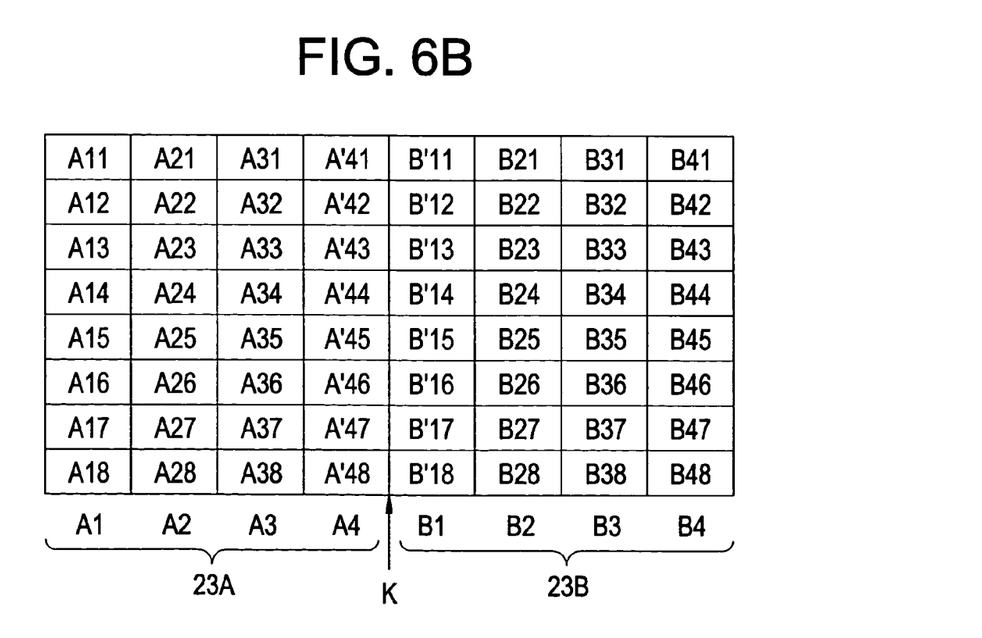

FIG. 6 is a diagram showing detection data generated based on an X-ray detected by sections of the two X-ray detection modules 23A and 23B, of the X-ray detector array 23 employed in the present embodiment, corresponding to A and B, which are arranged in parallel adjacent to each other in the body axial direction z, wherein FIG. 6(a) shows the data prior to the fitting processing, and FIG. 6(b) illustrates the data subsequent to the fitting processing. FIG. 6 shows sections in which the two X-ray detection modules 23A and 23B respectively have eight X-ray detection elements 23a arranged in the channel direction x and four X-ray detection elements 23a arranged in the body axial direction z. Incidentally, spots surrounded by rectangles in FIG. 6(a) show first detection data A41 through A48 and B11 through B18 obtained by the X-ray detected by X-ray detection elements 23a adjacent to a boundary K between the two X-ray detection modules 23A and 23B.

Figure 7A:
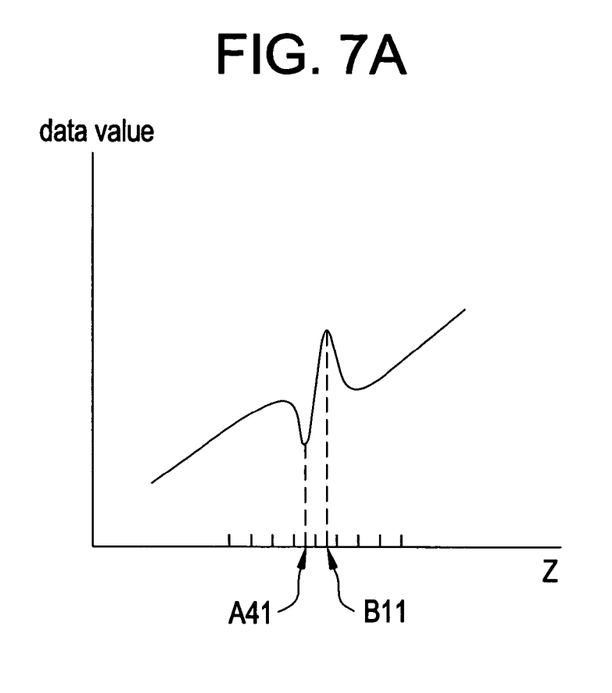
FIG. 7 is a plotted diagram of detection data obtained by the X-ray detection elements arranged in the body axial direction in the X-ray CT apparatus used as the radiation tomography apparatus according to the embodiment 1 of the present invention.
Figure 7B:
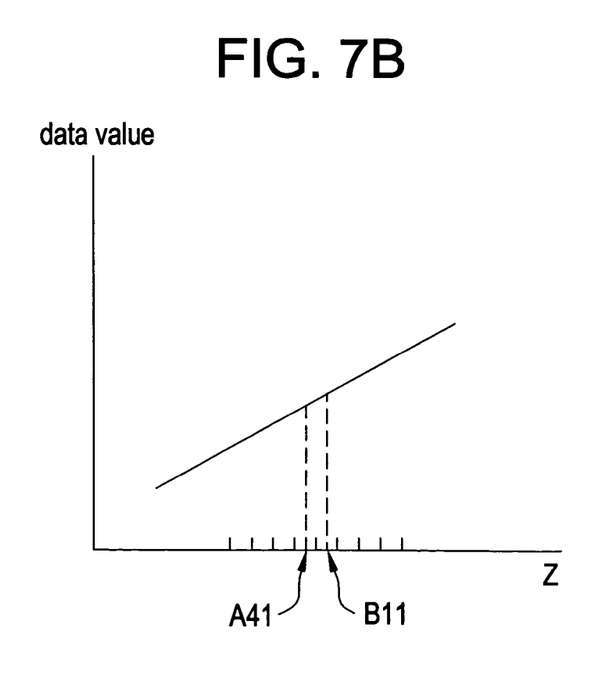

FIG. 7 is a plotted diagram of detection data obtained by the X-ray detection elements 23a arranged in the body axial direction in the present embodiment, wherein FIG. 7(a) shows the detection data prior to the fitting processing process, and FIG. 7(b) shows the detection data subsequent to the fitting processing process. Detection data A11, A21, A31, A41, B11, B21, B31 and B41 having first detection data and second detection data arranged in the body axial direction as shown in FIG. 6, for example, are used in FIG. 7. In FIG. 7, the horizontal axis indicates the position of each X-ray detection element 23a that obtains the detection data, and the vertical axis indicates data values of detection data generated based on the intensities of detected X-rays.

In the X-ray tomography method, an operator first inputs information about an imaging area of a subject 6 to be imaged to the central processing unit 30 via the input device 31 ahead of the scanning of an X-ray 5. Then the central processing unit 30 outputs a control signal CTL30b for carrying the imaging table 4 with the subject 6 placed thereon in the X-ray irradiation space 29 of the scanning gantry 2 or carrying out it therefrom to the imaging table 4 on the basis of the information inputted from the input device 31 and positions the imaging area of the subject 6 so that the imaging area thereof is placed in a desired position of the X-ray irradiation space 29 of the scanning gantry 2. Also the central processing unit 30 outputs a control signal CTL301 to the X-ray controller 25 and causes the X-ray controller 25 to output a control signal CTL251 to the X-ray tube 20, thereby executing radiation of X-ray 5 from the X-ray tube 20. Further, the central processing unit 30 outputs a control signal CTL302 to the collimator controller 26 and allows the collimator controller 26 to supply a control signal CTL261 for controlling the degree of opening of the aperture 221 of the collimator 22 to the collimator 22. An X-ray transmitted through the imaging area of the subject 6 is detected by the X-ray detector array 23 which includes the X-ray detection modules in which the X-ray detection elements 23a are disposed in array form, and wherein the X-ray detection modules are disposed adjacent to one another. Then the X-ray 5 detected by the X-ray detector array 23 is subjected to pre-treatment such as sensitivity correction to thereby produce detection data.

As shown in FIG. 7(a), waveform data based on the detection data A11, A21, A31, A41, B11, B21, B31 and B41 having the first detection data and second detection data are discontinuous at a portion between the first detection data A41 and B11. This cause results from the fact that since the portions equivalent to the first detection data A41 and B11 are obtained from X-rays detected by X-ray detection elements 23a adjacent to boundaries K between a plurality of X-ray detection modules 23A and 23B, the portions are different from the generated amount of crosstalk contained in the second detection data A11, A21, A31, B21, B31 and B41.

Thus, in order to correct the difference between the generated amounts of crosstalk that the first and second detection data contain as shown in FIG. 7, detection data are subjected to fitting processing in such a manner that, of the detection data generated by an X-ray detected by the X-ray detector array 23, first detection data generated by an X-ray detected by X-ray detection elements 23a adjacent to the boundaries between the plurality of X-ray detection modules 23A and 23B are adapted to waveform data based on second detection data generated by radiation detected by X-ray detection elements 23a lying around the X-ray detection elements 23a that obtain the first detection data, in a fitting processing process employed in the X-ray tomography method.

Here, fitting processing is performed using the first detection data and the second detection data in the fitting processing process employed in the present embodiment. For example, weighting factors are respectively given to the first detection data and the second detection data in such a manner that they are adapted to waveform data represented in a polynomial equation derived from a least squares error reference, using the first detection data and the second detection data, thereby performing polynomial equation fitting processing for normalizing the first detection data. As shown in FIG. 6, in order to cause first detection data A41 at one X-ray detection module 23A to adapt to waveform data expressed in second and tertiary polynomial equations, predetermined weighting factors are given to the first detection data A41 and detection data A11, A21, A31, B11, B21 and B31 obtained by three X-ray detection elements lying in the body axial direction with the first detection data A41 as the center and then added together as in the case of A'41= (−2·A11+3·A21+6·A31+7·A41+6·B11+3·B21−2·B31)/21, after which a value A'41 obtained by dividing the added value by a predetermined normalization factor is set as the first detection data A41. First detection data B11 at the other X-ray detection module 23B is similarly processed. Incidentally, the fitting processing process according to the present embodiment is synonymous with the fact that the first detection data and the second detection data are filtered using a low-pass filter and high-frequency components contained in the first detection data in large numbers are removed. A desired low-pass filter can be used according to diagnostic purposes and subject regions.

Thus, the first detection data A41 through A48 and B11 through B18 shown in FIG. 6(a) are substituted with their corresponding first detection data A'41 through A'48 and B'11 through B'18 corrected by the fitting processing as shown in FIG. 6(b). Further, the first detection data is corrected so as to adapt to the waveform data based on the second detection data as shown in FIG. 7(b).

In a tomographic image generating process, the central processing unit 30 performs an image reconstruction on the basis of the detection data subjected to the fitting processing to generate tomographic image data. In a display process, the central processing unit 30 causes the display device 32 to display the tomographic image generated in the tomographic image generating process.

In the present embodiment as mentioned above, an X-ray is applied to an imaging area of a subject to be imaged. The X-ray transmitted through the imaging area of the subject is detected by X-ray detection elements disposed in array form in a plurality of X-ray detection modules arranged adjacent to one another in a subject's body axial direction. Of detection data generated by the X-ray detected by the X-ray detection elements, first detection data generated by the X-ray detected by X-ray detection elements adjacent to boundaries among the plurality of X-ray detection modules are subjected to fitting processing so as to be adapted to waveform data based on second detection data generated by the X-ray detected by X-ray detection elements lying therearound as viewed in the subject's body axial direction.

Owing to the execution of the fitting processing, the first detection data detected by the X-ray detection elements lying in the neighborhood of the boundaries among the plural X-ray detection modules as viewed in the body axial direction are corrected so as to contain the generated amount of crosstalk where the data are not affected by the boundaries among the X-ray detection modules as viewed in the body axial direction. That is, the first detection data are corrected such that profiles of the generated amount of crosstalk as viewed in the body axial direction become continuous. In the present embodiment, the first detection data are corrected based on detection data obtained upon imaging of the imaging area of the subject without using the predetermined generated amount of crosstalk. Therefore, the present embodiment is capable of providing high-accuracy correction, preventing a reduction in the contrast of a tomographic image and the occurrence of artifacts and improving the quality of a tomographic image generated by reconstruction.

In the present embodiment as well, fitting processing is carried out through the use of polynomial fitting processing using first detection data and second detection data. Since the fitting processing is done by such a simplified method, a subject can be imaged at high speed.

Embodiment 2

An X-ray CT apparatus used as a radiation tomography apparatus according to an embodiment 2 of the present invention has such configurations as shown in FIGS. 1 and 2 in a manner similar to the embodiment 1. The X-ray CT apparatus according to the present embodiment is similar to the embodiment 1 except that a fitting processing means is different from that employed in the embodiment 1. Therefore, the description of parts common to the X-ray CT apparatus according to the embodiment 1 will be omitted.

The fitting processing means of the X-ray CT apparatus according to the present embodiment is provided in a central processing unit 30 in a manner similar to the embodiment 1. In the present embodiment, the fitting processing means calculates dummy data corresponding to first detection data according to fitting processing using only second detection data and substitutes the dummy data with the first detection data.

An X-ray tomography method using the X-ray CT apparatus according to the present embodiment will next be described. The X-ray tomography method according to the present embodiment is similar to the embodiment 1 except that the present embodiment is different in fitting processing process from the embodiment 1. The description of parts common to the X-ray tomography method according to the embodiment 1 will therefore be omitted.

Figure 8A:
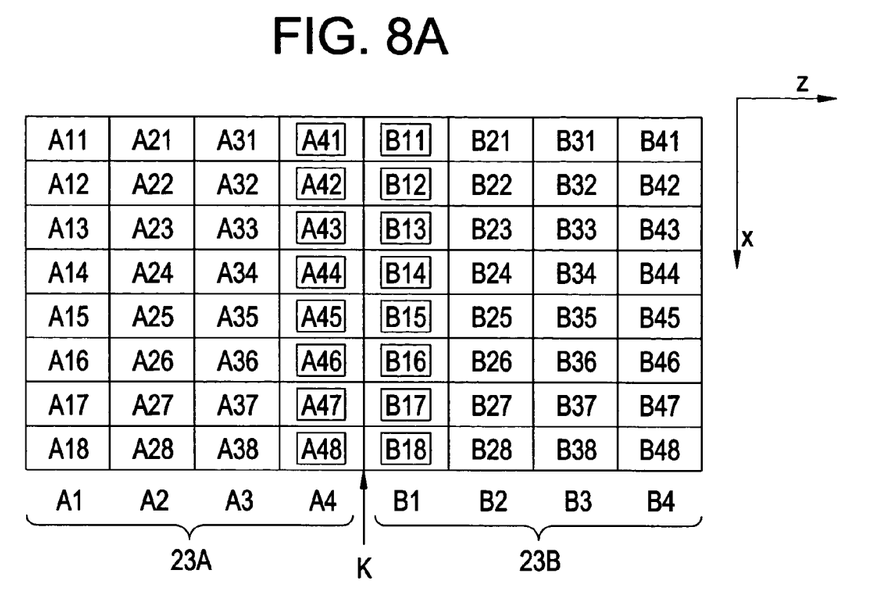
FIG. 8 is a diagram showing detection data generated by an X-ray detected by sections of two X-ray detection modules corresponding to A and B, of a plurality of X-ray detection modules in an X-ray detector array employed in an X-ray CT apparatus used as a radiation tomography apparatus according to an embodiment 2 of the present invention, which two modules are arranged in parallel adjacent to each other as viewed in a body axis direction.
Figure 8B:
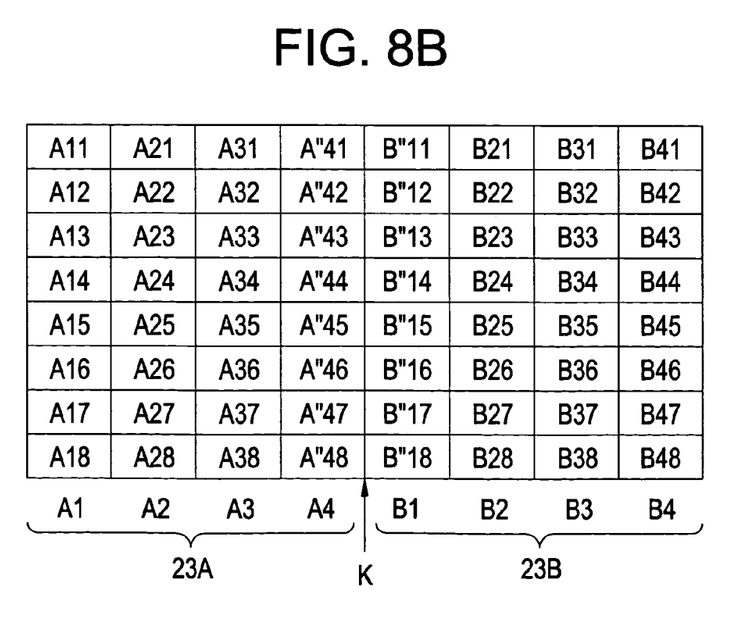

FIG. 8 is a diagram showing detection data generated by an X-ray detected by portions or sections of two X-ray detection modules 23A and 23B corresponding to A and B, of an X-ray detector array 23 according to the present embodiment, which modules are arranged in parallel adjacent to each other as viewed in a body axis direction z, wherein FIG. 8(a) shows the data prior to fitting processing, and FIG. 8(b) shows the data subsequent to the fitting processing. FIG. 8 shows sections in which the two X-ray detection modules 23A and 23B respectively have eight X-ray detection elements 23a arranged in a channel direction x and four X-ray detection elements 23a arranged in the body axial direction z. Incidentally, spots surrounded by rectangles in FIG. 8(a) show first detection data A41 through A48 and B11 through B18 obtained by the X-ray detected by the X-ray detection elements 23a adjacent to a boundary K between the two X-ray detection modules 23A and 23B.

A fitting processing process according to the present embodiment calculates dummy data corresponding to first detection data according to fitting processing using only second detection data and substitutes the dummy data with the first detection data. As shown in FIG. 8(a), for example, second detection data A11, A21, A31, B21, B31 and B41 are subjected to filtering processing using a low-pass filter to derive waveform data based on the second detection data A11, A21, A31, B21, B31 and B41. As shown in FIG. 8(b), dummy data A"41 and B"11 corresponding to the first detection data A41 and B1 are calculated using the waveform data, and then substituted with the first detection data A41 and B11 to thereby execute fitting processing.

In the present embodiment as described above, the dummy data corresponding to the first detection data are calculated according to the fitting processing using only the second detection data and thereafter substituted with the first detection data. Therefore, the present embodiment is capable of preventing a reduction in the contrast of a tomographic image and the occurrence of artifacts, improving the quality of a tomographic image generated by reconstruction, and providing high-speed imaging in a manner similar to the embodiment 1.

Embodiment 3

An X-ray CT apparatus used as a radiation tomography apparatus according to an embodiment 3 of the present invention has such configurations as shown in FIGS. 1 and 2 in a manner similar to the embodiments 1 and 2. The X-ray CT apparatus according to the present embodiment is similar to the embodiments 1 and 2 except that a fitting processing means is different from ones employed the embodiments 1 and 2. Therefore, the description of parts common to the X-ray CT apparatuses according to the embodiments 1 and 2 will be omitted.

The fitting processing means of the X-ray CT apparatus according to the present embodiment is provided in a central processing unit 30 in a manner similar to the embodiments 1 and 2. In the present embodiment, the fitting processing means calculates first dummy data corresponding to first detection data according to fitting processing using second detection data by means of a plurality of X-ray detection modules respectively and calculates differential data between the first dummy data and the first detection data by means of the plurality of X-ray detection modules respectively. Further, average data of differential data are respectively calculated by the plurality of X-ray detection modules, and second dummy data corresponding to the difference between the first data and the differential average data is calculated by each of the plurality of X-ray detection modules. Thereafter, the first detection data corresponding to the plurality of X-ray detection modules are substituted with the second dummy data.

An X-ray tomography method using the X-ray CT apparatus according to the present embodiment will next be described. The X-ray tomography method according to the present embodiment is similar to the embodiments 1 and 2 except that the present embodiment is different in fitting processing process from the embodiments 1 and 2. The description of parts common to the X-ray tomography methods according to the embodiments 1 and 2 will therefore be omitted.

Figure 9A:
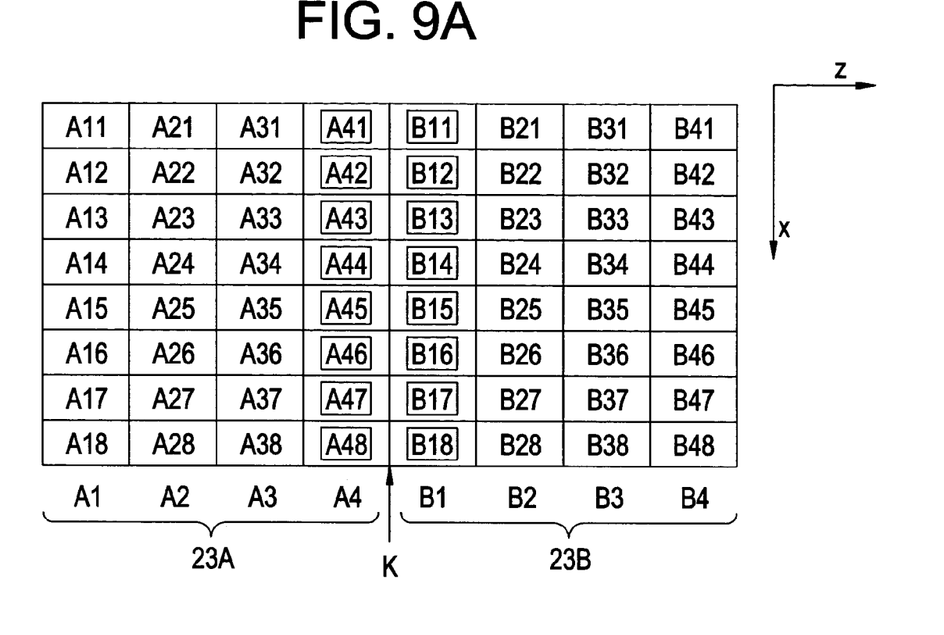
FIG. 9 is a diagram showing detection data generated by an X-ray detected by sections of two X-ray detection modules corresponding to A and B, of a plurality of X-ray detection modules in an X-ray detector array employed in an X-ray CT apparatus used as a radiation tomography apparatus according to an embodiment 3 of the present invention, which two modules are arranged in parallel adjacent to each other as viewed in a body axis direction.
Figure 9B:
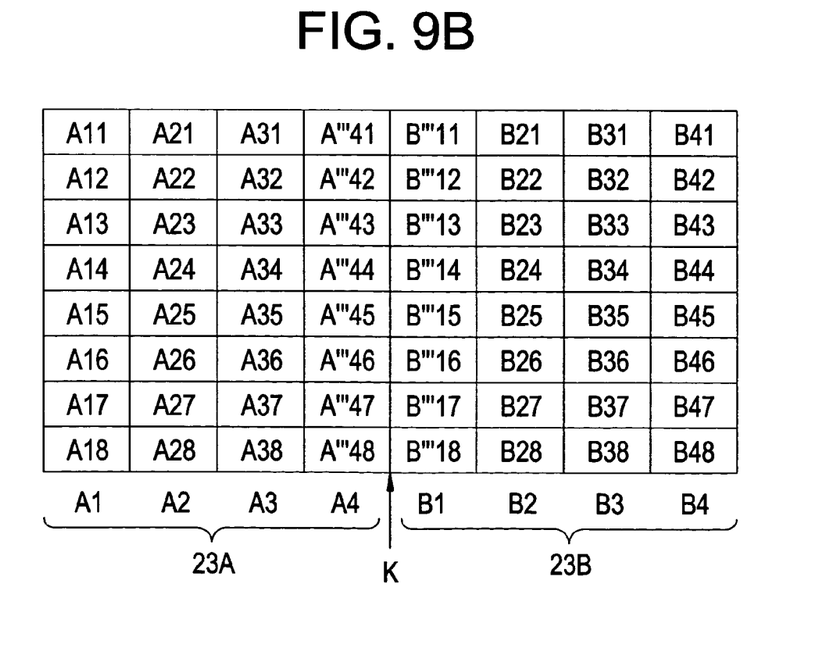

FIG. 9 is a diagram showing detection data generated by an X-ray detected by portions or sections of two X-ray detection modules 23A and 23B corresponding to A and B, of an X-ray detector array 23 according to the present embodiment, which modules are arranged in parallel adjacent to each other as viewed in a body axis direction z, wherein FIG. 9(a) shows the data prior to fitting processing, and FIG. 9(b) shows the data subsequent to the fitting processing. FIG. 9 shows sections in which the two X-ray detection modules 23A and 23B respectively have eight X-ray detection elements 23a arranged in a channel direction x and four X-ray detection elements 23a arranged in the body axial direction z. Incidentally, spots surrounded by rectangles in FIG. 9(a) show first detection data A41 through A48 and B11 through B18 obtained by the X-ray detected by the X-ray detection elements 23a adjacent to a boundary K between the two X-ray detection modules 23A and 23B.

The fitting processing process employed in the present embodiment calculates first dummy data corresponding to first detection data according to the fitting processing using the second detection data by means of the plurality of X-ray detection modules respectively and calculates differential data between the first dummy data and the first detection data by means of the plurality of X-ray detection modules respectively. Further, average data of the differential data are calculated by the plurality of X-ray detection modules respectively, and second dummy data corresponding to differences between the first data and the differential average data are calculated by the plurality of X-ray detection modules respectively. Thereafter, the first detection data corresponding to the plurality of X-ray detection modules are respectively substituted with the second dummy data.

As shown in FIG. 9, for example, second detection data A11, A21, A31, B21, B31 and B41 are subjected to filtering processing using a low-pass filter, followed by deriving of waveform data based on the second detection data A11, A21, A31, B21, B31 and B41 subjected to the filtering processing. Then, first detection data A41 detected by the X-ray detection module corresponding to a column A, and first dummy data A"41 and B"11 corresponding to the first detection data B11 detected by the X-ray detection module 23B corresponding to a column B are respectively calculated using the waveform data.

Thereafter, data AE41 and BE11 about differences between the first dummy data A"41 and B"11 and the first detection data A41 and B11 are calculated respectively. The differential data A41 and B11 are substantially equivalent to the generated amount of crosstalk where they are not affected by a boundary K between the X-ray detection modules 23A and 23B as viewed in the body axial direction. The above process is executed every X-ray detection elements 23a of the X-ray detection modules 23A and 23B to thereby calculate data AE41 through AE48 and BE11 through BE18 about differences between the first detection data A41 through A48 arranged in a channel direction x and first dummy data A'41 through A'48 and B'11 through B'18 respectively corresponding to the first detection data A41 through A48 and B11 through B18.

Differential average data AAE of the X-ray detection module 23A corresponding to the column A is calculated using the plurality of differential data AE48 through AE48 of the X-ray detection module 23A corresponding to the column A. Differential average data ABE of the X-ray detection module 23B corresponding to the column B is calculated using the plurality of differential data AE41 through AE48 and BE11 through BE18 of the X-ray detection module 23B corresponding to the column B.

Then, second dummy data A'''41 through A'''48 and B'''11 through B'''18 respectively corresponding to differences between the first detection data A41 through A48 and B11 through B18 and the differential average data AAE and ABE are calculated by the X-ray detection modules 23A and 23B corresponding to A and B respectively.

Thereafter, as shown in FIG. 9(b), the first detection data A41 through A48 and B11 through B18 respectively corresponding to the X-ray detection modules 23A and 23B corresponding to A and B are substituted with their corresponding second dummy data A'''41 through A'''48 and B'''11 through B'''18.

In the present embodiment as described above, differential data each substantially equivalent to the generated amount of crosstalk where they are not affected by boundaries among a plurality of X-ray detection modules as viewed in a body axial direction are averaged to determine or obtain differential average data, and the determined differential average data are used. Therefore, even if noise components are contained in the differential data, first detection data detected by X-ray detection elements in the vicinity of the boundaries among the plurality of X-ray detection modules as viewed in the body axial direction are corrected so as to contain the generated amount of crosstalk where they are not affected by the boundaries among the X-ray detection modules as viewed in the body axial direction, in a manner similar to second detection data lying therearound. It is thus possible to prevent a reduction in the contrast of a tomographic image and the occurrence of artifacts and improve the quality of the tomographic image in a manner similar to the embodiment 1.

Incidentally, the present invention is not limited to the above-described embodiments. Various modifications can be adopted.

Although detection data lying in the neighborhood of boundaries among a plurality of X-ray detection modules as viewed in a body axial direction are subjected to fitting processing in the present embodiment, for example, detection data in the neighborhood of boundaries among the plurality of X-ray detection modules as viewed in a channel direction may be applied.

Further, although detection data from first radiation detection elements corresponding to radiation detection elements most adjacent to a boundary between radiation detection modules are used as first detection data, and detection data from second radiation detection elements corresponding to radiation detection elements lying around first radiation detection elements, which are arranged three in a body axial direction, are used as second detection data, both the first detection data and the second detection data may use an arbitrary number of detection data, based on waveform data corresponding to the whole detection data.

Many widely different embodiments of the invention may be constructed without departing from the spirit and the scope of the present invention. It should be understood that the present invention is not limited to the specific embodiments described in the specification, except as defined in the appended claims.

The invention claimed is:

1. A radiation tomography apparatus, comprising:
   a radiation irradiating device for irradiating an imaging area of a subject to be imaged with radiation;
   a radiation detecting device having first and second radiation detection modules in which radiation detection elements detecting the radiation transmitted through the imaging area of the subject are arranged in array form, said first and second radiation detection modules being arranged adjacent to each other;
   a plurality of first radiation detection elements of said radiation detection elements, wherein the first radiation detection elements of said first radiation detection module are positioned adjacent said first radiation detection elements of said second radiation detection module, said first radiation detection elements configured to produce first detection data;
   a plurality of second radiation detection elements of said radiation detection elements positioned around said plurality of first radiation detection elements and configured to produce second detection data;
   a fitting processing device for fitting the first detection data to a continuity of the second detection data.

2. A radiation tomography apparatus according to claim 1, wherein the fitting processing device calculates dummy data corresponding to the first detection data according to fitting processing using only the second detection data, substitutes the dummy data for the first detection data, and fits the dummy data to a continuity of the second detection data.

3. A radiation tomography apparatus according to claim 1, wherein the fitting processing device is configured to:
   calculate first dummy data corresponding to the first detection data for each of said plurality of first radiation detection elements according to the fitting processing using the second detection data;
   calculate data corresponding to differences between the first dummy data and the first detection data for each of said plurality of first radiation detection elements;
   calculate average data of the differential data by the first and second radiation detection modules;
   calculate second dummy data corresponding to differences between the first data and the differential average data by the first and second radiation detection modules; and
   substitute the first detection data corresponding to the first and second radiation detection modules with the second dummy data.

4. A radiation tomography apparatus according to claim 1, wherein the fitting processing device performs polynomial fitting processing as the fitting processing.

5. A radiation tomography apparatus according to claim 1, further comprising a tomographic image generating device for generating tomographic image data of the imaging area of the subject, based on the detection data subjected to the fitting processing.

6. A radiation tomography apparatus according to claim 5, further comprising a display device for displaying a tomographic image, based on the tomographic image data generated by the tomographic image generating device.

7. A radiation tomography apparatus according to claim 1, wherein the radiation irradiating device applies an X-ray as the radiation.

8. A radiation tomography method using a radiation tomography apparatus having a radiation irradiating device for irradiating an imaging area of a subject to be imaged with radiation, and a radiation detecting device having first and second radiation detection modules in which radiation detection elements detecting the radiation transmitted through the imaging area of the subject are arranged in array form, said first and second radiation detection modules being arranged adjacent to each other, said radiation tomography method comprising:
   producing first detection data using a plurality of first radiation detection elements of the radiation detection elements, wherein the first radiation detection elements of said first radiation detection module are positioned adjacent said first radiation detection elements of said second radiation detection module;
   producing second detection data using a plurality of second radiation detection elements of the radiation detection elements positioned around the plurality of first radiation detection elements;
   fitting the first detection data to a continuity of the second detection data; and
   generating tomographic image data based on the fitting processing.

9. A radiation tomography method according to claim 8, further comprising:
   calculating dummy data corresponding to the first detection data by fitting processing using the second detection data; and
   substituting the calculated dummy data for the first detection data and fitting the dummy data to a continuity of the second detection data.

10. A radiation tomography method according to claim 8 further comprising:
    calculating first dummy data corresponding to the first detection data for each of the plurality of first radiation detection elements according to the fitting processing using the second detection data;
    calculating data corresponding to differences between the first dummy data and the first detection data for each of the plurality of first radiation detection elements;
    calculating average data of the differential data by the first and second radiation detection modules;
    calculating second dummy data corresponding to differences between the first data and the differential average data by the first and second radiation detection modules; and
    substituting the first detection data corresponding to the first and second radiation detection modules with the second dummy data.

11. A radiation tomography method according to claim 8, wherein fitting the first detection data to the second detection data further comprises fitting the first detection data to the second detection data using polynomial fitting processing.

12. A radiation tomography method according to claim 8, further comprising displaying a tomographic image based on the tomographic image data.

13. A radiation tomography method according to claim 8, wherein an X-ray is applied as the radiation.

* * * * *